US011000263B2

(12) United States Patent
Sato

(10) Patent No.: US 11,000,263 B2
(45) Date of Patent: May 11, 2021

(54) ULTRASOUND DIAGNOSTIC APPARATUS, IMAGE PROCESSING DEVICE, AND IMAGE PROCESSING METHOD

(71) Applicant: Toshiba Medical Systems Corporation, Otawara (JP)

(72) Inventor: Takeshi Sato, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1088 days.

(21) Appl. No.: 14/738,979

(22) Filed: Jun. 15, 2015

(65) Prior Publication Data

US 2015/0282787 A1 Oct. 8, 2015

Related U.S. Application Data

(63) Continuation of application No. PCT/JP2014/051301, filed on Jan. 22, 2014.

(30) Foreign Application Priority Data

Jan. 23, 2013 (JP) .............................. JP2013-010456
Jan. 22, 2014 (JP) .............................. JP2014-009850

(51) Int. Cl.
*A61B 8/06* (2006.01)
*G01S 15/89* (2006.01)
(Continued)

(52) U.S. Cl.
CPC .............. *A61B 8/5246* (2013.01); *A61B 8/06* (2013.01); *A61B 8/14* (2013.01); *A61B 8/463* (2013.01);
(Continued)

(58) Field of Classification Search
CPC ......... G01S 15/8981; A61B 8/06; A61B 8/14; A61B 8/488; A61B 8/5207
See application file for complete search history.

(56) References Cited

U.S. PATENT DOCUMENTS

| 5,249,578 A | 10/1993 | Karp et al. |
| 2008/0242982 A1* | 10/2008 | Tamura .................... A61B 8/06 600/441 |
| 2012/0130249 A1* | 5/2012 | Lee .................... G01N 29/0654 600/454 |

FOREIGN PATENT DOCUMENTS

| JP | 7-59771 A | 3/1995 |
| JP | 8-168489 A | 7/1996 |

(Continued)

OTHER PUBLICATIONS

Kadi et al., On the Performance of Regression and Step-Initialized IIR Clutter Filters for Color Doppler Systems in Diagnostic Medical Ultrasound, IEEE Transactions on Ultrasonics, Ferroelectrics, and Frequency Control, vol. 42, No. 5, Sep. 1995.*

(Continued)

*Primary Examiner* — Jason M Ip
(74) *Attorney, Agent, or Firm* — Oblon, McClelland, Maier & Neustadt, L.L.P.

(57) ABSTRACT

An ultrasound diagnostic apparatus of an embodiment includes filter processing circuitry, setting circuitry, an estimation circuitry, image generation circuitry, and control circuitry. The filter processing circuitry uses, as input data, a data array of reflected wave data of the same location collected by transmitting/receiving ultrasound multiple times and performs filter processing on the input data to output data, as output data, in which a clutter component is suppressed. The setting circuitry sets a correction value on the basis of a power value of the input data and a power value of the output data. The estimation circuitry acquires corrected blood flow information by using the output data and the correction value. The image generation circuitry generates ultrasound image data on the basis of the blood flow information. The control circuitry causes the ultrasound image data to be displayed in a display.

10 Claims, 10 Drawing Sheets

(51) Int. Cl.
  *A61B 8/00* (2006.01)
  *A61B 8/08* (2006.01)
  *A61B 8/14* (2006.01)

(52) U.S. Cl.
  CPC ............ *A61B 8/488* (2013.01); *A61B 8/5207* (2013.01); *G01S 15/8981* (2013.01)

(56) References Cited

FOREIGN PATENT DOCUMENTS

| | | |
|---|---|---|
| JP | 11-267125 A | 10/1999 |
| JP | 2010-522582 A | 7/2010 |

OTHER PUBLICATIONS

International Search Report dated Feb. 18, 2014 for PCT/JP2014/051301 filed on Jan. 22, 2014 in English Language.

Bjaerum, S., et al., "Clutter Filters Adapted to Tissue Motion in Ultrasound Color Flow Imaging," *IEEE Transactions on Ultrasonics, Ferroelectrics, and Frequency Control*, vol. 49, No. 6, Jun. 2002, pp. 693-704.

\* cited by examiner

Max Filter

ULTRASOUND DIAGNOSTIC APPARATUS, IMAGE PROCESSING DEVICE, AND IMAGE PROCESSING METHOD

CROSS-REFERENCE TO RELATED APPLICATIONS

This application is a continuation of PCT international application Ser. No. PCT/JP2014/051301 filed on Jan. 22, 2014 which designates the United States, the entire contents of which are incorporated herein by reference, and which claims the benefit of priority from Japanese Patent Application No. 2013-010456, filed on Jan. 23, 2013, and Japanese Patent Application No. 2014-009850, filed on Jan. 22, 2014; the entire contents of which are incorporated herein by reference.

FIELD

Embodiments described herein relate generally to an ultrasound diagnostic apparatus, an image processing device, and an image processing method.

BACKGROUND

An ultrasound diagnostic apparatus has been widely used to observe and diagnose a blood flow in a living body. The ultrasound diagnostic apparatus employs a Doppler method based on a Doppler effect to generate and display blood flow information from a reflected wave of ultrasound. The blood flow information generated and displayed by the ultrasound diagnostic apparatus includes a color Doppler image and a Doppler waveform (Doppler spectrum).

The color Doppler image is an ultrasound image visualized by a color flow mapping (CFM) method. The CFM method performs transmission/reception of ultrasound multiple times on a plurality of scanning lines. The CFM method then applies an MTI (Moving Target Indicator) filter to a data array of the same location and extracts a signal derived from the blood flow while suppressing a signal (clutter signal) derived from a stationary tissue or a slow-moving tissue. The CFM method uses this blood flow signal to estimate blood flow information such as velocity, variance and power of the blood flow, thereby displaying an ultrasound image (blood flow image or color Doppler image) in which the distribution of the estimation result is displayed in color and in two dimensions, for example. The blood flow information is usually displayed superposed on a B-mode image (tissue image). The blood flow image is displayed in a region where there is a blood flow, while the B-mode image is displayed in a region where there is no blood flow, for example. Therefore, one is required to perform processing of determining whether there is a blood flow when displaying the blood flow image.

The most popular method of performing such determination processing is a method of determining a blood flow signal as noise and not displaying the image when a power value of the blood flow signal is lower than or equal to a predetermined fixed value. Suppressed by the MTI filter to have a small value, the clutter signal is not displayed by the determination processing using the power value. However, a signal from a tissue of a strong reflector such as an organ wall or a bone has a large amplitude and may remain after passing the MTI filter even though the movement of the tissue is slow. In such case, the signal from the strong reflector is displayed as though it is the blood flow.

Accordingly, there is known a method of checking the velocity of an output signal and, when the velocity is slow, determining that the output signal is not derived from the blood flow and not displaying the signal. Such method is effective to some extent for the following reason when a Butterworth IIR (Infinite Impulse Response) filter having an HPF (High Pass Filter) characteristic is used as the MTI filter. That is, when the packet size has a finite length requiring a transient response measure, the signal from the strong reflector remains since the characteristic of the IIR filter is unfavorable. This causes the average velocity within the packet to slow down, the average velocity being lower than or equal to a lower threshold corresponding to a velocity of non-display.

In recent years, there has been used as the MTI filter a polynomial regression filter and an "Eigenvector Regression Filter" being an adaptive MTI filter. These filters can efficiently suppress the clutter signal with a small packet size compared to the Butterworth IIR filter. That is, these filters can suppress the signal from the strong reflector to a level corresponding to the blood flow signal. There is however a limit to the clutter suppression capability, where these filters cannot suppress the signal from the strong reflector to a level of noise. While the Butterworth filter has a linear phase characteristic, the polynomial regression filter and "Eigenvector Regression Filter" do not have the linear phase characteristic. Accordingly, when the velocity is estimated from the output signal from these filters, an estimated velocity of a slow signal such as the clutter signal tends to have a relatively high value so that there has been a case where the signal from the strong reflector remains to display an image indicating that there is a blood flow in a tissue of the strong reflector even when the slow signal is eliminated by the aforementioned method.

DETAILED DESCRIPTION

An ultrasound diagnostic apparatus of an embodiment includes filter processing circuitry, setting circuitry, an estimation circuitry, image generation circuitry, and control circuitry. The filter processing circuitry is configured to use, as input data, a data array of reflected wave data of the same location collected by transmitting/receiving ultrasound multiple times and perform filter processing on the input data to output output data in which a clutter component is suppressed. The setting circuitry is configured to set a correction value on the basis of a power value of the input data and a power value of the output data. The estimation circuitry is configured to acquire corrected blood flow information by using the output data and the correction value. The image generation circuitry is configured to generate ultrasound image data on the basis of the blood flow information. The control circuitry is configured to cause the ultrasound image data to be displayed in a display.

Embodiments of an ultrasound diagnostic apparatus will now be described in detail with reference to the drawings.

Embodiments

Figure 1:
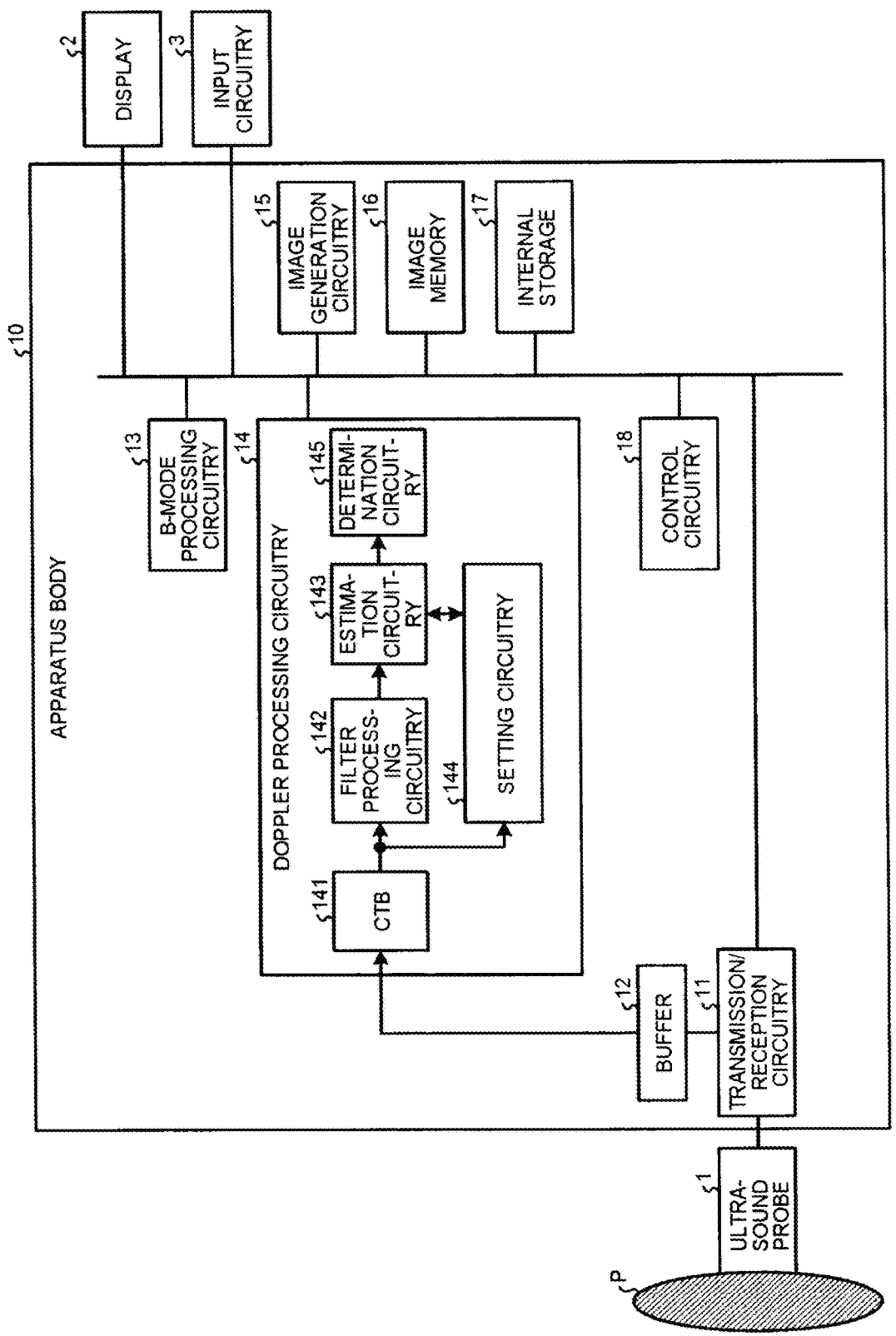
FIG. 1 is a block diagram illustrating an example of a configuration of an ultrasound diagnostic apparatus according to the present embodiment.

First, a configuration of an ultrasound diagnostic apparatus according to the present embodiment will be described. FIG. 1 is a block diagram illustrating an example of the configuration of the ultrasound diagnostic apparatus according to the present embodiment. As illustrated in FIG. 1, the ultrasound diagnostic apparatus according to the present embodiment includes an ultrasound probe 1, a display 2, an input circuitry 3, and an apparatus body 10.

The ultrasound probe 1 is connected to the apparatus body 10 to transmit/receive ultrasound thereto/therefrom. The ultrasound probe 1 includes a plurality of piezoelectric transducer elements which generates ultrasound on the basis of a drive signal supplied from transmission/reception circuitry 11 (to be described) included in the apparatus body 10. The plurality of piezoelectric transducer elements included in the ultrasound probe 1 also receives a reflected wave from a subject P and converts it into an electrical signal. The ultrasound probe 1 further includes a matching layer provided to the piezoelectric transducer element and a backing material that prevents the propagation of ultrasound to the back of the piezoelectric transducer element. The ultrasound probe 1 is detachably connected to the apparatus body 10.

When transmitted from the ultrasound probe 1 to the subject P, the ultrasound is reflected one after another off of a surface having a discontinuous acoustic impedance in an in vivo tissue of the subject P and is received as a reflected wave signal by the plurality of piezoelectric transducer elements included in the ultrasound probe 1. The amplitude of the received reflected wave signal depends on the difference in the acoustic impedance on the discontinuous surface from which the ultrasound is reflected. The reflected wave signal generated when the transmitted ultrasound pulse is reflected off of a blood flow in motion or a surface such as a cardiac wall is subjected to a frequency shift by a Doppler effect while depending on a velocity component of a moving body with respect to a direction in which the ultrasound is transmitted.

The present embodiment is applicable when the ultrasound probe 1 is either a 1D array probe which two-dimensionally scans the subject P or a mechanical 4D probe or 2D array probe which three-dimensionally scans the subject P.

The input circuitry 3 includes a mouse, a keyboard, a button, a panel switch, a touch command screen, a foot switch, a track ball, and a joystick. The input circuitry 3 receives various setting requests from an operator of the ultrasound diagnostic apparatus and transfers the various setting requests received to the apparatus body 10.

The display 2 displays a GUI (Graphical User Interface) provided for the operator of the ultrasound diagnostic apparatus to input the various setting requests by using the input circuitry 3, and displays ultrasound image data generated in the apparatus body 10, for example.

The apparatus body 10 generates the ultrasound image data on the basis of the reflected wave signal received by the ultrasound probe 1. The apparatus body 10 illustrated in FIG. 1 can generate two-dimensional ultrasound image data on the basis of a two-dimensional reflected wave signal and three-dimensional ultrasound image data on the basis of a three-dimensional reflected wave signal. The present embodiment is also applicable to the apparatus body 10 that is adapted specifically for the two-dimensional data.

As illustrated in FIG. 1, the apparatus body 10 includes the transmission/reception circuitry 11, a buffer 12, B-mode processing circuitry 13, Doppler processing circuitry 14, image generation circuitry 15, an image memory 16, an internal storage 17, and control circuitry 18.

The transmission/reception circuitry 11 controls ultrasound transmission/reception performed by the ultrasound probe 1 on the basis of an instruction from the control circuitry 18 to be described. The transmission/reception circuitry 11 includes a pulse generator, transmission delay circuitry, a pulser and the like and supplies a drive signal to the ultrasound probe 1. The pulse generator repeatedly generates a rate pulse to form a transmission ultrasound at a predetermined pulse repetition frequency (PRF). The transmission delay circuitry focuses the ultrasound generated from the ultrasound probe 1 into a beam and applies, to each rate pulse generated by the pulse generator, a delay time for each piezoelectric transducer element required to determine transmission directivity. The pulser impresses a drive signal (drive pulse) on the ultrasound probe 1 at a timing based on the rate pulse. That is, the transmission delay circuitry varies the delay time applied to each rate pulse to adjust at will the direction of the ultrasound transmitted from the surface of the piezoelectric transducer element.

The transmission/reception circuitry 11 has a function that can instantaneously change a transmission frequency and a transmitted drive voltage to execute a predetermined scan sequence on the basis of an instruction from the control circuitry 18 to be described. In particular, the transmitted drive voltage can be changed by transmission circuitry of a linear amplifier type that can instantaneously switch the value or by a mechanism that electrically switches a plurality of power supply units.

The transmission/reception circuitry 11 also includes amplifier circuitry, an A/D (Analog/Digital) converter, reception delay circuitry, an adder, and quadrature detection circuitry and generates reflected wave data by performing various processing on the reflected wave signal received by the ultrasound probe 1. The amplifier circuitry performs gain correction by amplifying the reflected wave signal for each channel. The A/D converter performs A/D conversion on the gain-corrected reflected wave signal. The reception delay circuitry applies to digital data a reception delay time required to determine reception directivity. The adder adds the reflected wave signal to which the reception delay time is applied by the reception delay circuitry. The addition performed by the adder enhances a reflection component from a direction corresponding to the reception directivity of the reflected wave signal.

The quadrature detection circuitry converts an output signal of the adder into an in-phase signal (I signal, I: In-phase) and a quadrature signal (Q signal, Q: Quadrature-phase) in the baseband. The quadrature detection circuitry then stores the I signal and Q signal (hereinafter noted as an IQ signal) as reflected wave data into the buffer 12. The quadrature detection circuitry may also convert the output signal of the adder into an RF (Radio Frequency) signal and store it into the buffer 12.

When performing the two-dimensional scan on the subject P, the transmission/reception circuitry 11 causes the ultrasound probe 1 to transmit a two-dimensional ultrasound beam. The transmission/reception circuitry 11 then generates two-dimensional reflected wave data from a two-dimensional reflected wave signal received by the ultrasound probe 1. When performing the three-dimensional scan on the subject P, the transmission/reception circuitry 11 causes the ultrasound probe 1 to transmit a three-dimensional ultrasound beam. The transmission/reception circuitry 11 then generates three-dimensional reflected wave data from a three-dimensional reflected wave signal received by the ultrasound probe 1.

The buffer 12 temporarily stores the reflected wave data (I/Q signal) generated by the transmission/reception circuitry 11. Specifically, the buffer 12 stores the I/Q signal corresponding to the number of frames or the I/Q signal corresponding to the number of volumes. The buffer 12 is an FIFO (First-In/First-Out) memory, for example, and stores the I/Q signal corresponding to a predetermined number of frames. When the transmission/reception circuitry 11 newly generates an I/Q signal corresponding to one frame, for example, the buffer 12 discards the I/Q signal corresponding to the oldest frame in terms of the time generated and stores the I/Q signal corresponding to the one frame newly generated.

The B-mode processing circuitry 13 and the Doppler processing circuitry 14 are signal processing circuitry that perform various signal processings on the reflected wave data generated from the reflected wave signal by the transmission/reception circuitry 11. The B-mode processing circuitry 13 performs logarithmic amplification, envelope detection, and logarithmic compression on the reflected wave data (I/Q signal) read from the buffer 12 and generates data (B-mode data) by which the signal strength of each of a plurality of sample points is expressed by a degree of brightness.

The Doppler processing circuitry 14 performs a frequency analysis on the reflected wave data read from the buffer 12 and generates data (Doppler data) that is formed by extracting motion information based on the Doppler effect of a moving body within a scanning range. Specifically, the Doppler processing circuitry 14 generates the Doppler data at each of the plurality of sample points by extracting an average velocity, an average variance, and an average power value as the motion information of the moving body. The moving body in this case refers to a blood flow, a tissue such as a cardiac wall, and a contrast agent, for example. The Doppler processing circuitry 14 according to the present embodiment estimates at each of the plurality of sample points an average velocity of the blood flow, an average variance of the blood flow, and an average power value of the blood flow as the motion information of the blood flow (blood flow information). The Doppler processing circuitry 14 then outputs the estimated blood flow information as the Doppler data.

Using the function of the Doppler processing circuitry 14, the ultrasound diagnostic apparatus according to the present embodiment can execute a color Doppler method also referred to as a color flow mapping (CFM) method. The CFM method performs transmission/reception of ultrasound multiple times on a plurality of scanning lines. A data array of the reflected wave signal (reflected wave data) from the same location acquired by the ultrasound transmission/reception is called a packet. A packet size corresponds to the number of ultrasound transmission/reception performed in the same direction to acquire the blood flow information of a single frame.

The CFM method then applies an MTI (Moving Target Indicator) filter to a data array of the same location and extracts a signal derived from the blood flow while suppressing a signal (clutter signal) derived from a stationary tissue or a slow-moving tissue. Then from the blood flow signal, the CFM method estimates the blood flow information such as the velocity of the blood flow, the variance of the blood flow, and the power of the blood flow. The image generation circuitry 15 to be described generates ultrasound image data (color Doppler image data) which two-dimensionally displays the distribution of the estimation result in color, for example. The display 2 thereafter displays the color Doppler image data.

The Doppler processing circuitry 14, for generating the Doppler data, includes a CTB 141, filter processing circuitry 142, estimation circuitry t 143, and determination circuitry 145. The CTB 141 is a "Corner Turning Buffer" which temporarily stores a time-series data array of the reflected wave data from the buffer 12. Specifically, the CTB 141 rearranges and stores the data array of the reflected wave data for each scanning line in the order of the time series such that processing in the following stage is executed smoothly. Such rearrangement is performed by a control circuit (not shown) which receives an instruction from the control circuitry 18 to be described, for example.

The filter processing circuitry 142 performs the MTI filter processing on the data array of the same location that is the input data to output output data in which a clutter component is suppressed. The output data is a piece of data in which the blood flow component is extracted. The estimation circuitry 143 estimates the blood flow information from the output data. The determination circuitry 145 determines whether the blood flow information is derived from the blood flow or the tissue. The determination circuitry 145 outputs the blood flow information determined to be derived from the blood flow as the Doppler data.

The Doppler processing circuitry 14 of the present embodiment further includes setting circuitry 144 as illustrated in FIG. 1. The setting circuitry 144 sets a correction value (correction coefficient) used to perform the gain correction on the blood flow information. The setting circuitry 144 sets the correction value by calculation, for example. The processing performed by the setting circuitry 144 will be described later in detail along with the processing performed by each of the filter processing circuitry 142, the estimation circuitry 143, and the determination circuitry 145.

Here, the B-mode processing circuitry 13 and the Doppler processing circuitry 14 illustrated in FIG. 1 can perform processing on both the two-dimensional reflected wave data and the three-dimensional reflected wave data. That is, the B-mode processing circuitry 13 generates two-dimensional B-mode data from the two-dimensional reflected wave data and three-dimensional B-mode data from the three-dimensional reflected wave data. The Doppler processing circuitry 14 generates two-dimensional Doppler data from the two-dimensional reflected wave data and three-dimensional Doppler data from the three-dimensional reflected wave data.

The image generation circuitry 15 generates the ultrasound image data from the data generated by the B-mode processing circuitry 13 and the Doppler processing circuitry 14. The image generation circuitry 15 generates two-dimensional B-mode image data, representing the strength of the reflected wave by the brightness, from the two-dimensional B-mode data generated by the B-mode processing circuitry 13. Moreover, the image generation circuitry 15 generates two-dimensional Doppler image data, which is the visualization of the blood flow information, from the two-dimensional Doppler data generated by the Doppler processing circuitry 14. The two-dimensional Doppler image data is velocity image data, variance image data, power image data, or a combination of these image data. The image generation circuitry 15 generates the color Doppler image data displaying the blood flow information in color as the Doppler image data, or generates the Doppler image data displaying one piece of blood flow information in gray scale.

Generally, the image generation circuitry 15 converts (scan converts) a scanning line signal string of ultrasound scan into a scanning line signal string of a video format typified by a television, and generates the ultrasound image data for display. Specifically, the image generation circuitry 15 performs coordinate conversion according to a scan mode of the ultrasound of the ultrasound probe 1 and then generates the ultrasound image data for display. In addition to the scan conversion, the image generation circuitry 15 uses a plurality of image frames after the scan conversion to perform various image processings such as image processing (smoothing processing) which regenerates an average value image of the brightness and image processing (edge enhancement processing) which uses a differential filter within the image, for example. The image generation circuitry 15 further superposes character information of various parameters, a scale, and a body mark on the ultrasound image data.

That is, the B-mode data and the Doppler data are the ultrasound image data before scan converted, while the data generated by the image generation circuitry 15 is the ultrasound image data for display after scan converted. The B-mode data and the Doppler data are also referred to as raw data. The image generation circuitry 15 generates the two-dimensional ultrasound image data for display from the two-dimensional ultrasound image data before scan conversion.

Moreover, the image generation circuitry 15 performs coordinate conversion on the three-dimensional B-mode data generated by the B-mode processing circuitry 13 and generates the three-dimensional B-mode image data. In addition, the image generation circuitry 15 performs coordinate conversion on the three-dimensional Doppler data generated by the Doppler processing circuitry 14 and generates the three-dimensional Doppler image data. The image generation circuitry 15 generates the "three-dimensional B-mode image data and three-dimensional Doppler image data" as "three-dimensional ultrasound image data (volume data)".

The image generation circuitry 15 further performs rendering on the volume data in order to generate various two-dimensional image data used to display the volume data on the display 2. The image generation circuitry 15 performs the rendering by, for example, performing a multi planer reconstruction (MPR) method to generate MPR image data from the volume data. The image generation circuitry 15 also performs the rendering by performing volume rendering (VR) which generates two-dimensional image data reflecting three-dimensional information, for example.

The image memory 16 stores the image data for display generated by the image generation circuitry 15. The image memory 16 can also store data generated by the B-mode processing circuitry 13 and the Doppler processing circuitry 14. The B-mode data and Doppler data stored in the image memory 16 can be called up by an operator after a diagnosis, for example, and becomes ultrasound image data for display through the image generation circuitry 15. The image memory 16 can also store the reflected wave data output by the transmission/reception circuitry 11.

The internal storage 17 stores a control program, diagnostic information (such as a patient ID and an observation by a doctor), and various data such as a diagnostic protocol and various body marks, the control program being used to perform ultrasound transmission/reception, image processing and display processing. Moreover, the internal storage 17 is used to retain the image data stored in the image memory 16 as needed. The data stored in the internal storage 17 can also be transferred to an external device via an interface not shown. Moreover, the internal storage 17 can store data transferred from the external device via the interface not shown.

The control circuitry 18 controls the entire processing of the ultrasound diagnostic apparatus. Specifically, the control circuitry 18 controls processing performed by the transmission/reception circuitry 11, the B-mode processing circuitry 13, the Doppler processing circuitry 14 and the image generation circuitry 15 on the basis of various setting requests input by the operator through the input circuitry 3 as well as various control programs and various data read from the internal storage 17. The control circuitry 18 controls ultrasound scanning by controlling the ultrasound probe 1 through the transmission/reception circuitry 11.

The control circuitry 18 further performs control such that the ultrasound image data for display stored in the image memory 16 and the internal storage 17 is displayed on the display 2. The transmission/reception circuitry 11 and the like included in the apparatus body 10 may be configured by hardware such as an integrated circuit or by software in the form of a module program.

The overall configuration of the ultrasound diagnostic apparatus according to the present embodiment has been described. With such configuration, the ultrasound diagnostic apparatus according to the present embodiment employs the CFM method to generate and display blood flow image data (Doppler image data). The Doppler image data generated by the CFM method is usually displayed superposed on the B-mode image data in which the morphology of a tissue is rendered. The scanning range of the Doppler mode is set within the scanning range of the B-mode, for example. In the superposed display, for example, Doppler image data is displayed in a region where there is a blood flow within the scanning range of the Doppler mode, while B-mode image data is displayed in a region where there is no blood flow within the scanning range. Therefore, one is required to perform processing of determining whether there is a blood flow when displaying the Doppler image data.

Figure 2A:
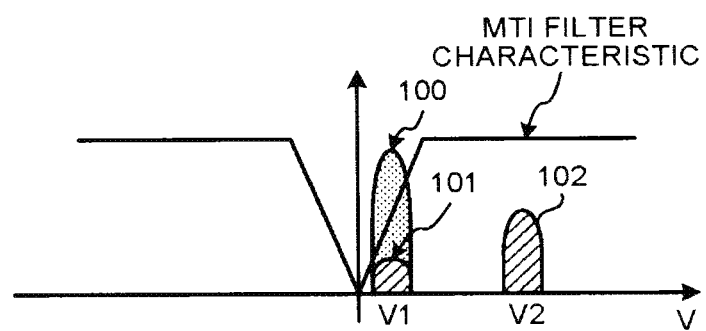
FIG. 2A, FIG. 2B, and FIG. 3 are diagrams provided to describe the related art.
Figure 2B:
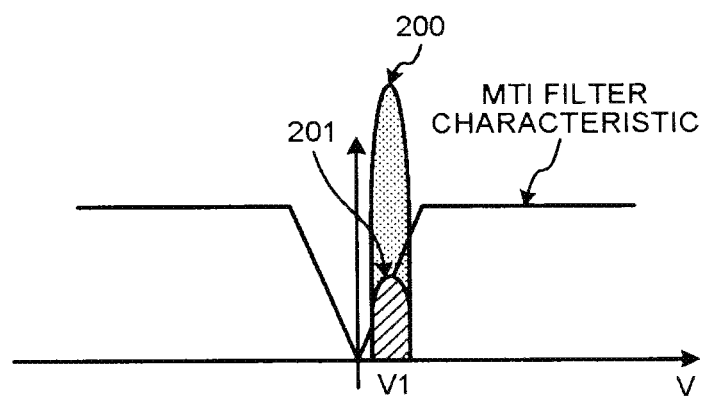
Figure 3:
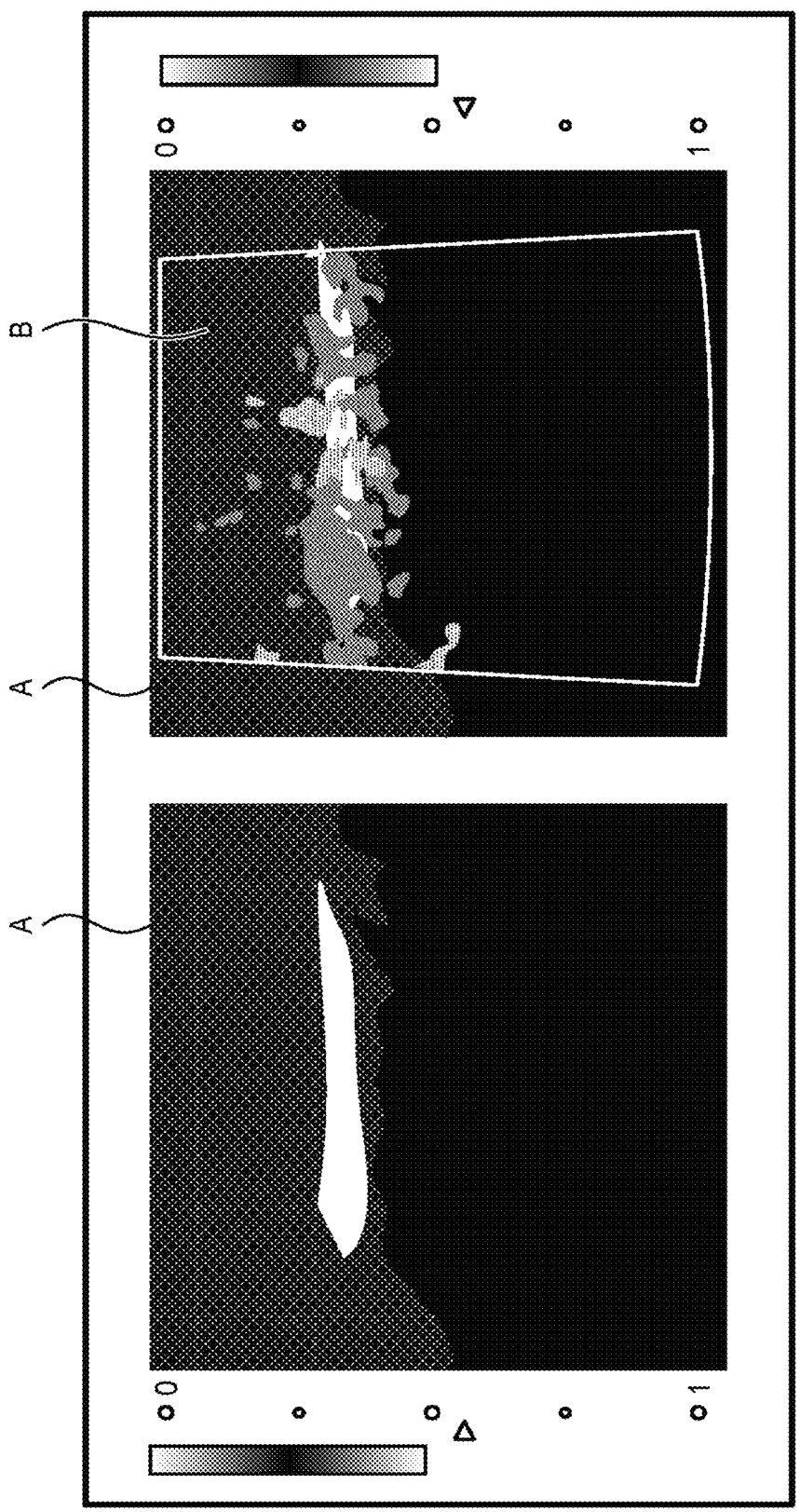

The most popular method of performing such determination processing is a method of determining a blood flow signal as noise and not displaying the image when a power value of the blood flow signal is lower than or equal to a predetermined fixed value. Suppressed by the MTI filter to have a small value, the clutter signal is not displayed by the determination processing using the power value. However, a signal from a tissue of a strong reflector such as an organ wall or a bone has a large amplitude and therefore may remain after passing the MTI filter even though the movement of the tissue is slow. In such case, the signal from the strong reflector is displayed as though it is the blood flow. FIGS. 2A, 2B, and 3 are diagrams provided to describe a related art.

FIGS. 2A and 2B illustrate a case of using an MTI filter having an MTI filter characteristic that has the clutter suppression capability of "−60 dB" for a slow velocity "V1" lower than or equal to a cut-off frequency. A signal 100 illustrated in FIG. 2A indicates a signal from a tissue that has the amplitude intensity of "20 dB" with respect to the amplitude intensity of the blood flow (0 dB) as a reference, the tissue moving at the velocity "V1". The signal 100 passes through the MTI filter and then becomes a signal 101, the amplitude intensity of which is suppressed to "−40 dB". As a result, the signal 101 is not extracted as a signal derived from the blood flow. A signal 102 illustrated in FIG. 2A indicates a signal from a blood flow that is moving at a velocity "V2" higher than or equal to the cut-off frequency of the MTI filter and has the amplitude intensity of "0 dB". The signal 102 passes through the MTI filter and is then output as a signal, the amplitude intensity of which is identical to that before input (0 dB). That is, the signal 102 is extracted as a signal derived from the blood flow.

On the other hand, a signal 200 illustrated in FIG. 2B indicates a signal from a tissue that has the amplitude intensity of "60 dB" with respect to the amplitude intensity of the blood flow (0 dB) as a reference, the tissue moving at the velocity "V1". The signal 200 passes through the MTI filter and is then output a signal 201, the amplitude intensity of which is suppressed to "0 dB". As a result, the signal 201 remains after passing through the MTI filter. In this case, an output signal from a wall has the same magnitude as an output signal from the blood flow, for example, so that the signal from the wall is displayed as though it is the blood flow.

Accordingly, there is known a method of checking not the power value but the velocity of the output signal of the MTI filter and, when the velocity is slow, determining that the output signal is not derived from the blood flow and not displaying the signal. Such method is effective to some extent for the following reason when a Butterworth IIR (Infinite Impulse Response) filter is used as the MTI filter installed in the filter processing circuitry 142. When the packet size has a finite length requiring a transient response measure, the signal from the strong reflector remains due to an unfavorable characteristic of the IIR filter. This causes the average velocity within the packet to slow down, the average velocity being lower than or equal to a lower threshold corresponding to a velocity of non-display.

On the other hand, in recent years, there has been used as the MTI filter a polynomial regression filter and an "Eigenvector Regression Filter" being an adaptive MTI filter. The MTI filter being a HPF used to suppress the clutter can adopt various filters which have the following advantage. Compared to the Butterworth IIR filter, these filters can efficiently suppress the clutter signal with a period longer than the packet length. That is, these filters can suppress the signal from the strong reflector to a level corresponding to the blood flow signal. There is however a limit to the clutter suppression capability, where these filters cannot suppress the signal from the strong reflector to a level of noise.

While the output of the Butterworth filter has the same phase characteristic, the output of the polynomial regression filter and "Eigenvector Regression Filter" has a different phase characteristic for each data. Therefore, the velocity estimated from the output signal of these filters is not accurate. When data of the wall of a slow-moving tissue after passing the MTI filter is used to estimate the velocity by an autocorrelation method, for example, a velocity faster than the actual motion of the tissue is detected. As a result, the signal from the strong reflector remains even when the signal with low velocity is excluded by the aforementioned method, thereby causing a case where there is displayed image data having a blood flow in a tissue of the strong reflector.

A left figure in FIG. 3 illustrates B-mode image data A of a fingertip displayed on a screen of the display 2. As illustrated in the left figure in FIG. 3, a phalanx being a strong reflector is rendered with high brightness in the B-mode image data A. A right figure in FIG. 3 illustrates Doppler image data B displayed superposed on the B-mode image data A of the fingertip. The Doppler image data B is generated and displayed by using the "Eigenvector Regression Filter", for example. As illustrated in the right figure in FIG. 3, a signal from the phalanx being the strong reflector is rendered as though it is the blood flow in the Doppler image data B. Use of the MTI filter with unfixed phase characteristic as described above sometimes causes a case where there is generated/displayed the Doppler image data in which a noise misidentified as the blood flow is rendered around the strong reflector. Such noise is clearly generated when the ultrasound probe 1 is moved regardless of whether the phase characteristic of the MTI filter is fixed or not.

Now, the ultrasound diagnostic apparatus according to the present embodiment performs the following processing by the Doppler processing circuitry 14 in order to avoid a case where the signal derived from the tissue of the strong reflector is displayed as the blood flow. An image processing method described below is a method of avoiding the case where a tissue signal from the strong reflector such as the wall of an organ or a bone is misidentified as the blood flow. In particular, the following image processing method is effective when one cannot identify by the power value or velocity of the output data whether a component is derived from the blood flow or the strong reflector because the polynomial regression filter or the "Eigenvector Regression Filter" with unfixed phase characteristic is used as the MTI filter. The following image processing method is also applicable to the MTI filter such as an IIR type filter with the fixed phase characteristic.

First, the filter processing circuitry 142 uses, as input data, a data array of the reflected wave data of the same location collected by transmitting/receiving the ultrasound multiple times, filters the input data to output output data in which the clutter component is suppressed. The filter processing circuitry 142 uses the "Eigenvector Regression Filter" as the MTI filter, for example.

Then, the setting circuitry 144 sets a correction value on the basis of the power value of the input data and the power value of the output data. The setting circuitry 144 according to the present embodiment calculates the correction value by using the power value of the input data and the power value of the output data. Specifically, the setting circuitry 144 according to the present embodiment sets the correction value on the basis of a ratio of the power value of the input data to the power value of the output data. More specifically, the setting circuitry 144 calculates a ratio obtained by dividing the power value of the input data by the power value of the output data. It is defined for example that "C" being a piece of information including the clutter is the power value of the input data while "D" being a piece of information extracted on the basis of the Doppler effect is the power value of the output data. The setting circuitry 144 calculates the correction value on the basis of "CDR=C/D".

As suggested by the relationship between the signal 201 and the signal 200 illustrated in FIG. 2B, the input data is considered to be derived from the reflected wave signal having the slow-moving strong reflector as a source of reflection, when "CDR=C/D" is large. In other words, it is highly likely that the output data is the remnant of the clutter component when the CDR is large. The present embodiment calculates the correction value which suppresses the output data when the CDR is large. This can prevent the misidentification of the strong reflector as the blood flow in the present embodiment. The present embodiment may also calculate the correction value from "CDR'=D/C" on the basis of the aforementioned logic. In this case, the correction value which suppresses the output data is calculated when CDR' is small.

Figure 4:
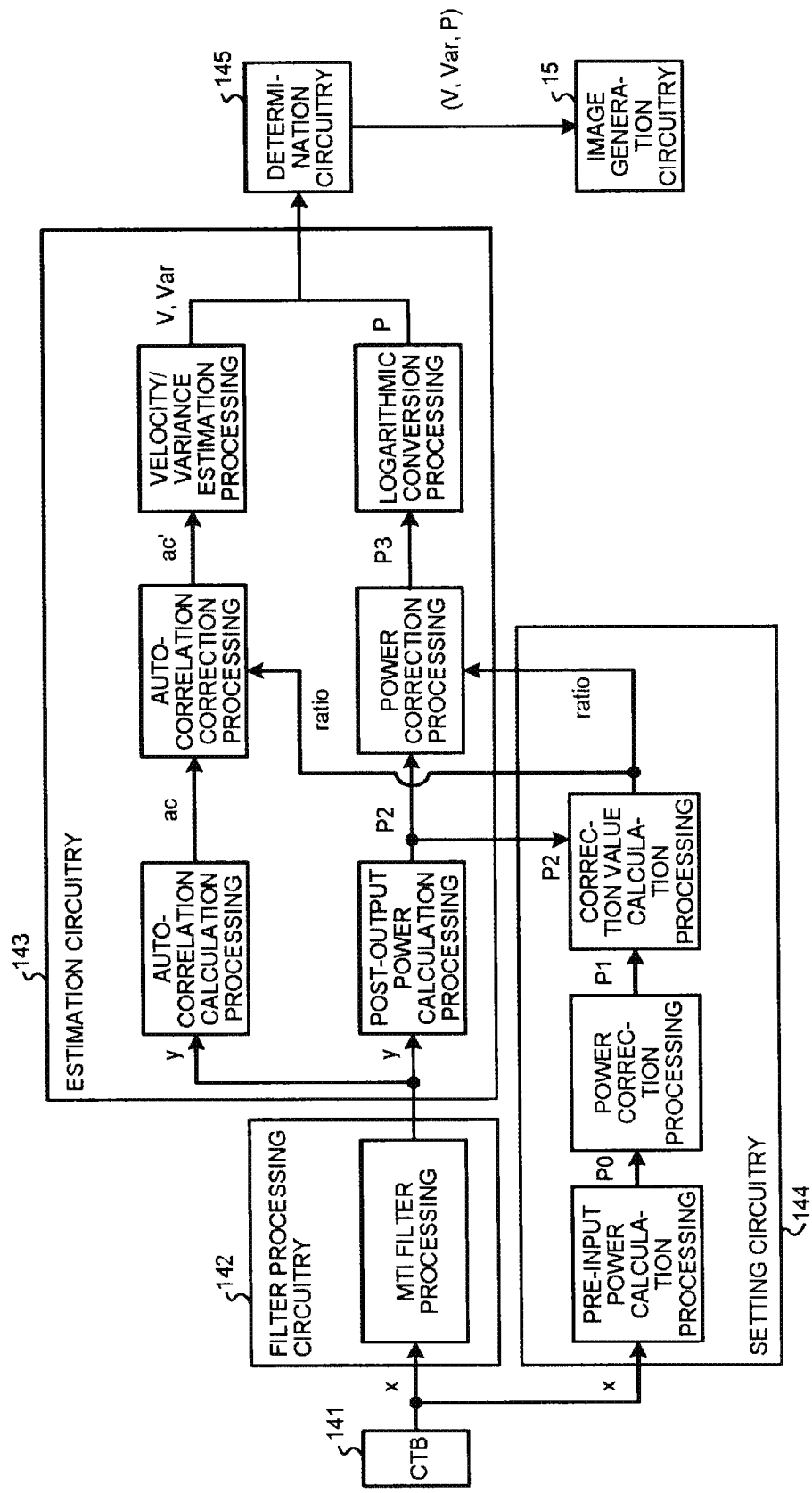
FIG. 4 is a diagram illustrating processing performed by Doppler processing circuitry according to the present embodiment.

The estimation circuitry 143 then uses the output data and the correction value to find corrected blood flow information. That is, the estimation circuitry 143 uses the output data and the correction value to estimate the blood flow information. The image generation circuitry 15 generates the ultrasound image data (Doppler image data) on the basis of the blood flow information, and the display 2 displays the ultrasound image data (Doppler image data) under control by the control circuitry 18. An example of the aforementioned processing will now be described with reference to FIG. 4. FIG. 4 is a diagram illustrating the processing performed by the Doppler processing circuitry according to the present embodiment.

First, as illustrated in FIG. 4, a data array "x" of the same location output from the CTB 141 is input to the filter processing circuitry 142 and the setting circuitry 144. The "x" indicates the input data. The input data "x" is hereinafter referred to as an input data array.

In an "MTI filter processing" block corresponding to the filter processing circuitry 142 illustrated in FIG. 4, the MTI filter is applied to the input data array "x" to output a data array "y" in which the clutter component is suppressed. The "y" indicates the output data. The output data "y" is hereinafter referred to as an output data array.

At the same time, in a "pre-input power calculation processing" block corresponding to the setting circuitry 144 illustrated in FIG. 4, a power value "P0" of the input data is calculated from the input data array "x". The setting circuitry 144 calculates an average power value of the input data array "x" or a maximum power value of the input data array "x" as the power value "P0". Here, it is preferred to have large "CDR" in order to surely prevent the misidentification of the strong reflector as the blood flow. The power value "P0" is preferably the maximum power value of the input data array "x". Accordingly, the setting circuitry 144 uses the maximum value of the power value of the input data to set the correction value. In the present embodiment, the setting circuitry 144 uses the maximum value of the power value of the input data to calculate the correction value. Note that the present embodiment may also be adapted to use a second largest power value of the input data array "x" and the like, to calculate the correction value.

The setting circuitry 144 calculates the maximum value of the power value "P0" of the input data by using the following expression (1).

$$P0 = \max\{x \cdot (k)x(k)\} \, k=1 \ldots N \quad (1)$$

In expression (1), "N" indicates the packet size, and "x(k)" indicates k-th data in N pieces of data constructing the input data array "x". An integer of 1 to N is denoted as "k". Moreover, in expression (1), a superscript asterisk "*" indicates a complex conjugate. A portion "x*(k)" in expression (1) corresponds to a complex conjugate value of "x(k)".

Here, "P0" may be input to a "correction value calculation processing" block of the setting circuitry 144 illustrated in FIG. 4, but is preferably input to a "power correction processing" block in FIG. 4 for the following reason.

When the reflected wave data (IQ signal) is generated from the reflected wave signal reflected off of the strong reflector, the reflected wave signal possibly saturates in the amplifier circuitry or A/D converter in some channel of the reception circuit of the transmission/reception circuitry 11. Signals from a plurality of channels including the signal from the saturated channel are input to the adder. However, an adder adapted to perform digital beam forming can possibly perform phasing and adding of a digital signal saturated at the positive maximum value and a digital signal saturated at the negative maximum value, for example. In this case, the amplitude of phased/added data output from the adder does not correspond to the saturated maximum amplitude. The maximum power value "P0" is possibly calculated from a saturated data array. In general, the reflected wave signal from the strong reflector such as the wall of an organ or bone is often saturated in the reception circuit of the transmission/reception circuitry 11 under a condition for the color Doppler. It is therefore assumed that a signal level input to the Doppler processing circuitry 14 is lower than an actual signal level.

In order to avoid the possibility that the value of the CDR is underestimated, the "power correction processing" block in FIG. 4 performs correction to increase the value of "P0" when the value of "P0" is larger than or equal to a threshold "Pth". A predetermined power value "Pth" can be set to any value by the operator or the like.

The setting circuitry 144 calculates a value "P1" that is the corrected value of "P0" by using the following expression (2), for example.

$$P1 = \begin{cases} P0 & (P0 < Pth) \\ P0 + (P0 - Pth)^n & (P0 \geq Pth) \end{cases} \quad (2)$$

In expression (2), "P0" is output as "P1" when "P0" is smaller than "Pth". Moreover, in expression (2), a value obtained by adding "a value obtained by raising "P0–Pth" to the power of "n"" to "P0" as "P1", when "P0" is larger than or equal to "Pth". Note that "n" is a real number of 1 or larger, preferably "n=2". Expression (2) merely being an example, the present embodiment can apply an arbitrary expression as long as the expression is used to perform correction that increases the value of "P0" when the value of "P0" is larger than or equal to the threshold "Pth".

Furthermore, the "power correction processing" block illustrated in FIG. 4 may be adapted to perform spatial correction after "correction of P0 by using Pth" or before "correction of P0 by using Pth" for the following reason.

An echo from the vicinity of the strong reflector has a medium signal level due to the effect of a side lobe of the ultrasound and is also susceptible to phase change. On the other hand, the MTI filter has a characteristic to enhance a signal undergoing the phase change. Therefore, the level of signal from the vicinity of the strong reflector that is not the blood flow may be increased after passing the MTI filter.

That is, when the vicinity of the strong reflector is the source of reflection, the denominator of the "CDR" has an increased value while the maximum power value "P0" calculated from the input data array "x" has a medium value. The value "P1" obtained by correcting "P0" may have a medium value as well. As a result, when the vicinity of the strong reflector is the source of reflection, the value of the "CDR" is possibly reduced to a degree not determined as a tissue. The vicinity of the strong reflector is also misidentified as the blood flow in this case.

Figure 5:
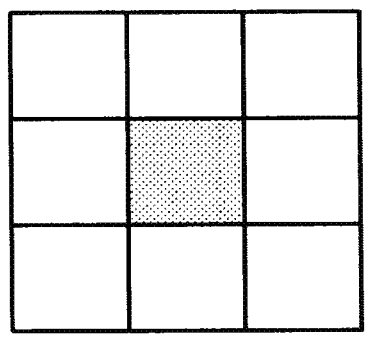
FIG. 5 is a diagram illustrating an example of a maximum value filter used by setting circuitry.

Accordingly, in the "power correction processing "block illustrated in FIG. 4, a spatial maximum value filter (Max Filter) is applied to "P0", for example. FIG. 5 is a diagram illustrating an example of the maximum value filter used by the setting circuitry 144. As illustrated in FIG. 5, for example, the setting circuitry 144 uses a "3×3" maximum value filter (Max Filter). That is, the setting circuitry 144 calculates the maximum power value of the input data at each of nine sample points in "3×3" centered around a sample point to be processed (refer to a hatched rectangle in FIG. 5). The setting circuitry 144 converts a pre-input power value of the sample point to be processed into a maximum power value among nine pre-input power values. The setting circuitry 144 then sets an output result of the maximum value filter to be the value of "P0" and outputs "P1" by using expression (2).

There has been described above the case where the maximum value filter is applied before the "correction of P0 by using Pth". On the other hand, the following processing is performed when the maximum value filter is applied after the "correction of P0 by using Pth". The setting circuitry 144 calculates a correction value for the maximum power value of the input data at each of the nine sample points in "3×3" centered around the sample point to be processed, for example. The setting circuitry 144 converts a correction value of the sample point to be processed into a maximum correction value among the nine pre-input power values. The setting circuitry 144 then sets an output result of the maximum value filter to be the value of "P1" and outputs "P1" to the following "correction value calculation processing" block. The setting circuitry 144 may apply a normal spatial smoothing filter instead of the maximum value filter. That is, the setting circuitry 144 corrects the pre-input power value to a statistic of the pre-input power value and an adjacent pre-input power value when performing spatial correction.

When the power value of the input data is larger than or equal to a predetermined power value, the setting circuitry 144 corrects the power value of the input data to a larger value, as described above. Moreover, the setting circuitry 144 corrects the power value of the input data to the statistic of the power value of the input data and a power value of input data in the vicinity of the input data. Both or either one of these two correction processings may be executed. When the correction is performed in the "power correction processing" block, the setting circuitry 144 sets the correction value by using the power value after correction and the power value of the output data. The setting circuitry 144 of the present embodiment calculates the correction value by using the power value after correction and the power value of the output data. Note that it may be adapted to not perform the correction in the "power correction processing" block in the present embodiment.

In parallel with the calculation of "P0" and "P1" performed by the setting circuitry 144, the output data array "y" output from the "MTI filter processing" block is used to calculate a power value "P2" of the output data in a "post-output power calculation processing" block of the estimation circuitry 143 illustrated in FIG. 4. The setting circuitry 144 calculates an average power value of the output data array "y" or a maximum power value of the output data array "y" as the power value "P2". The average power value of the output data array "y" is preferably set as the power value "P2" in terms of correcting the value of the CDR to a larger one to prevent the tissue from being displayed as the blood flow, and for the reason that a value used in a "logarithmic conversion processing" block of the estimation circuitry 143 in FIG. 4 is normally the average power value.

Accordingly, the estimation circuitry 143 calculates "P2" being the average value of the power value of the output data by using the following expression (3).

$$P2 = \frac{1}{N} \sum_{k=1}^{N} y^*(k) y(k) \qquad (3)$$

In expression (3), "y (k)" indicates k-th data in N pieces of data constructing "y". An integer of 1 to N is denoted as "k". The part "y (k)" in expression (3) corresponds to a complex conjugate value of "y (k)".

Note that in the present embodiment, the estimation circuitry 143 may also output the average value of the power value of the output data to the "logarithmic conversion processing" block and output the maximum value of the power value of the output data to the "correction value calculation processing" block of the setting circuitry 144 illustrated in FIG. 4". Moreover, as power correction processing is performed when the value of the CDR is large in the present embodiment, the estimation circuitry 143 may output not the average value of the power value of the output data but a median or minimum value of the power value of the output data to the "correction value calculation processing" block.

In parallel with the calculation of "P0" and "P1", an autocorrelation value "ac" of the output data array "y" output from the "MTI filter processing" block is calculated by the following expression (4) in an "autocorrelation calculation processing" block of the estimation circuitry 143 illustrated in FIG. 4.

$$ac = \frac{1}{N-1} \sum_{k=1}^{N-1} y^*(k) y(k+1) \qquad (4)$$

Then, P1 and P2 are used to calculate the correction value in the "correction value calculation processing" block of the setting circuitry 144 illustrated in FIG. 4.

The aforementioned calculation of "CDR" is performed first in the "correction value calculation processing" block. The setting circuitry 144 calculates "CDR" by using the following expression (5) while assuming "C=P1 and D=P2".

$$CDR = \frac{P1}{P2} \qquad (5)$$

The setting circuitry 144 in the "correction value calculation processing" block then calculates a correction value "ratio" used to correct "P2" and "ac" on the basis of "CDR". Specifically, when "CDR" is larger than or equal to a predetermined ratio "CDRth" set as a threshold, the correction value "ratio" which reduces the value of the blood flow information output by the estimation circuitry 143 is calculated. The ratio "CDRth" can be set to any value by the operator or the like.

The value "ratio" is a correction coefficient multiplied to each of "P2" and "ac". The setting circuitry 144 calculates "ratio" by using the following expression (6), for example.

$$\text{ratio} = \begin{cases} 1 & (CDR < CDRth) \\ \left(\dfrac{CDRth}{CDR}\right)^m & (CDR \geq CDRth) \end{cases} \quad (6)$$

Figure 6:
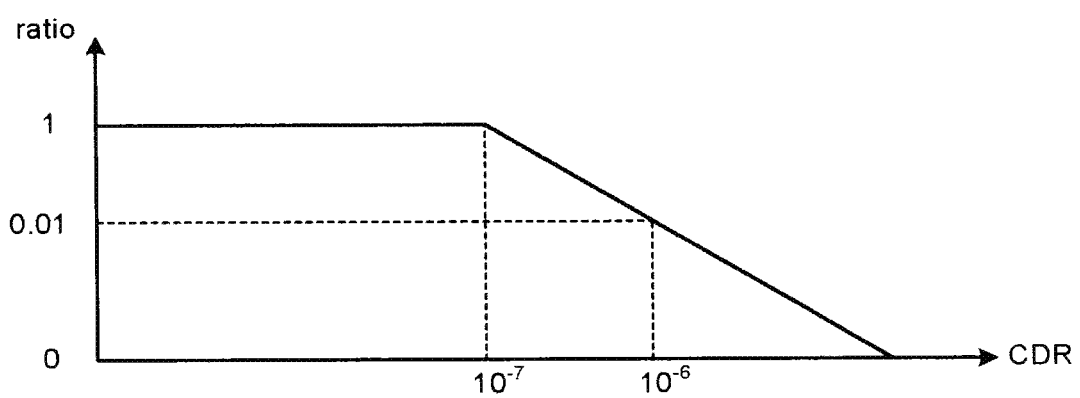
FIG. 6 is a graph illustrating an example of a correction value.

In expression (6), the correction value equals "ratio=1" when "CDR" is smaller than "CDRth". This means that "P2" and "ac" are not corrected when "CDR" is smaller than "CDRth". On the other hand, in expression (6), a "value obtained by raising "CDRth/CDR" to the power of "m"" is calculated as "ratio" when "CDR" is larger than or equal to "CDRth". Here, "m" is a real number of 1 or larger. The "m" is preferably set to around "2". The "m" can be set to any value by the operator or the like. FIG. 6 is a graph illustrating an example of the correction value.

FIG. 6 illustrates the example of "ratio" calculated when "m=2". In the graph illustrated in FIG. 6, a horizontal axis represents a value of "CDR" converted to a decibel form while a vertical axis represents "ratio". FIG. 6 illustrates the example of "ratio" calculated when "CDRth" equals "$10^{-7}$ (=−70 dB)". The decibel value of the CDR is obtained by a decibel formula used on power. When "CDR" is larger than or equal to "$10^{-7}$ (=−70 dB)", the output power value is decreased by "ratio" illustrated in FIG. 6.

As described with reference to FIG. 2B, for example, the signal 200 of the tissue having the amplitude intensity of "60 dB" is output as the signal 201, the amplitude intensity of which is suppressed to "0 dB", by the MTI filter having the clutter suppression capability of "−60 dB" for the slow velocity "V1" lower than or equal to the cut-off frequency. At this time, the CDR equals "CDR=−60 dB (=$10^{-6}$)". Moreover, the output power value of the signal 201 is decreased to "−20 dB" by "ratio=$(10^{-7}/10^{-6})^2$=0.01 (=−20 dB)" to a level lower than the blood flow signal. The decibel value of "ratio" is obtained by the decibel formula used on power.

Expression (6) merely being an example, any expression can be used to calculate "ratio" as long as the correction is performed to decrease the value of the blood flow information when "CDR" is larger than or equal to "CDRth". Moreover, the setting circuitry 144 of the present embodiment may be adapted to set the correction value by acquiring the correction value "ratio" while referring to a LUT (Look Up Table) in which a combination of the value of "CDR" and the value of "ratio" is set in advance. The setting circuitry 144 may also calculate the ratio "CDR'=D/C" obtained by dividing the power value of the output data by the power value of the input data as described above. In such variation, the setting circuitry 144 sets the correction value "ratio" which reduces the value of the blood flow information output by the estimation circuitry 143, when "CDR'" is smaller than or equal to a predetermined ratio "CDR'th". In such variation, for example, the setting circuitry 144 calculates the correction value "ratio" which reduces the value of the blood flow information output by the estimation circuitry 143, when "CDR'" is smaller than or equal to the predetermined ratio "CDR'th". Alternatively, in such variation, the setting circuitry 144 sets the correction value by acquiring the correction value "ratio" while referring to a LUT in which a combination of the value of "CDR'" and the value of "ratio" is set in advance.

Moreover, as a variation, the setting circuitry 144 of the present embodiment may set the correction value "ratio" which reduces the value of the blood flow information output by the estimation circuitry 143 when a logarithmic value "log CDR" is larger than or equal to a predetermined logarithmic value, the logarithmic value "log CDR" being calculated from the ratio "CDR" obtained by dividing the power value of the input data by the power value of the output data. This setting may be performed by referring to a LUT in which a combination of the value of "log CDR" and the value of "ratio" is set in advance, or by performing calculation using an expression to which "log CDR" is input to give "ratio". The setting circuitry 144 may also calculate "log CDR" by finding a difference "log P1−log P2".

Moreover, as a variation, the setting circuitry 144 of the present embodiment may set the correction value "ratio" which reduces the value of the blood flow information output by the estimation circuitry 143 when a logarithmic value "log CDR'" is smaller than or equal to a predetermined logarithmic value, the logarithmic value "log CDR'" being calculated from the ratio "CDR'" obtained by dividing the power value of the output data by the power value of the input data. This setting may be performed by referring to a LUT in which a combination of the value of "log CDR'" and the value of "ratio" is set in advance, or by performing calculation using an expression to which "log CDR'" is input to give "ratio". The setting circuitry 144 may also calculate "log CDR'" by finding a difference "log P2−log P1".

The setting circuitry 144 thereafter notifies the "autocorrelation correction processing" block and the "power correction processing" block of the estimation circuitry 143 in FIG. 4 of the calculated "ratio". The estimation circuitry 143 in the "power correction processing" block uses "P2" and "ratio" to calculate a corrected power value "P3" by the following expression (7).

$$P3 = P2 * \text{ratio} \quad (7)$$

The estimation circuitry 143 in the "autocorrelation correction processing" block uses "ac" and "ratio" to calculate a corrected autocorrelation value "ac'" by the following expression (8).

$$ac' = ac * \text{ratio} \quad (8)$$

The estimation circuitry 143 uses "P3" to calculate a power value "P" as the blood flow information by the following expression (9), in the "logarithmic conversion processing" block illustrated in FIG. 4.

$$P = 10 \log_{10}(P3) \quad (9)$$

Furthermore, the estimation circuitry 143 uses "ac'" to calculate velocity "V" and variance "Var" as the blood flow information by the following expression (10), in a "velocity/variance estimation processing" block illustrated in FIG. 4.

$$\left. \begin{array}{l} V = a\tan2(\text{imag}(ac'), \text{real}(ac')) \\ \text{Var} = 1 - \dfrac{|ac'|}{P3} \end{array} \right\} \quad (10)$$

Note that "a tan 2" in expression (10) is an "arc tangent function" outputting the angle of "−πn to +π", "imag" being an abbreviation of "imaginary part" is a function which outputs only an imaginary part from a complex number, and "real" is a function which outputs only a real part from the complex number.

The estimation circuitry 143 thereafter outputs the blood flow information "V, Var, P" to the determination circuitry 145. The estimation circuitry 143 performs the aforementioned processing for all the sample points.

The determination circuitry 145 determines whether or not to output the blood flow information "V, Var, P" input from the estimation circuitry 143 as Doppler data. The determination circuitry 145 excludes the blood flow information when the velocity "V" of the blood flow information is lower than a threshold "V #", for example. Alternatively, the determination circuitry 145 excludes the blood flow information when the power value "P" of the blood flow information is smaller than a threshold "P #", for example. Alternatively, the determination circuitry 145 excludes the blood flow information when the velocity "V" of the blood flow information is lower than the threshold "V #" or when the power value "P" of the blood flow information is smaller than the threshold "P #", for example.

The blood flow information output as the Doppler data from the determination circuitry 145 is generated as the Doppler image data by the image generation circuitry 15, whereby the Doppler image data is displayed on the display 2.

The effect of correction processing performed in the present embodiment will be described with reference to FIGS. 7 to 10. FIGS. 7 to 10 are diagrams provided to describe the effect of the present embodiment.

Figure 7:
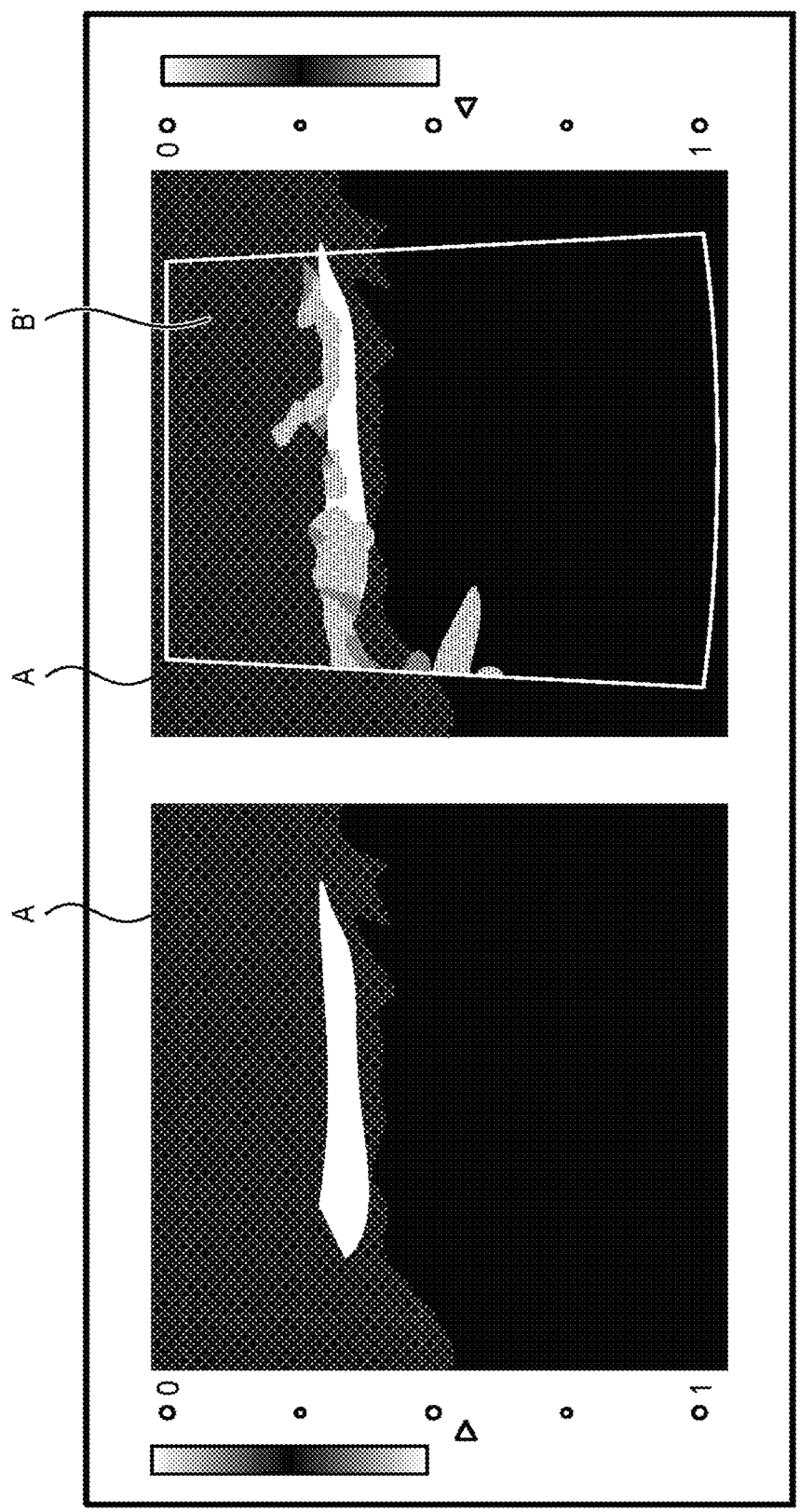
FIG. 7, FIG. 8, FIG. 9, and FIG. 10 are diagrams provided to describe the effect of the present embodiment.

FIG. 7 will be described. A left figure in FIG. 7 illustrates the B-mode image data A of the fingertip as illustrated in FIG. 3. A right figure in FIG. 7 illustrates Doppler image data B' displayed on top of the B-mode image data A of the fingertip. The Doppler image data B' is generated and displayed by the correction processing described with reference to FIG. 4 and the like. Compared to the Doppler image data B illustrated in FIG. 3, the "noise around the strong reflector" generated in the Doppler image data B in FIG. 3 is eliminated from the Doppler image data B' as illustrated in the right figure in FIG. 7.

Figure 8:
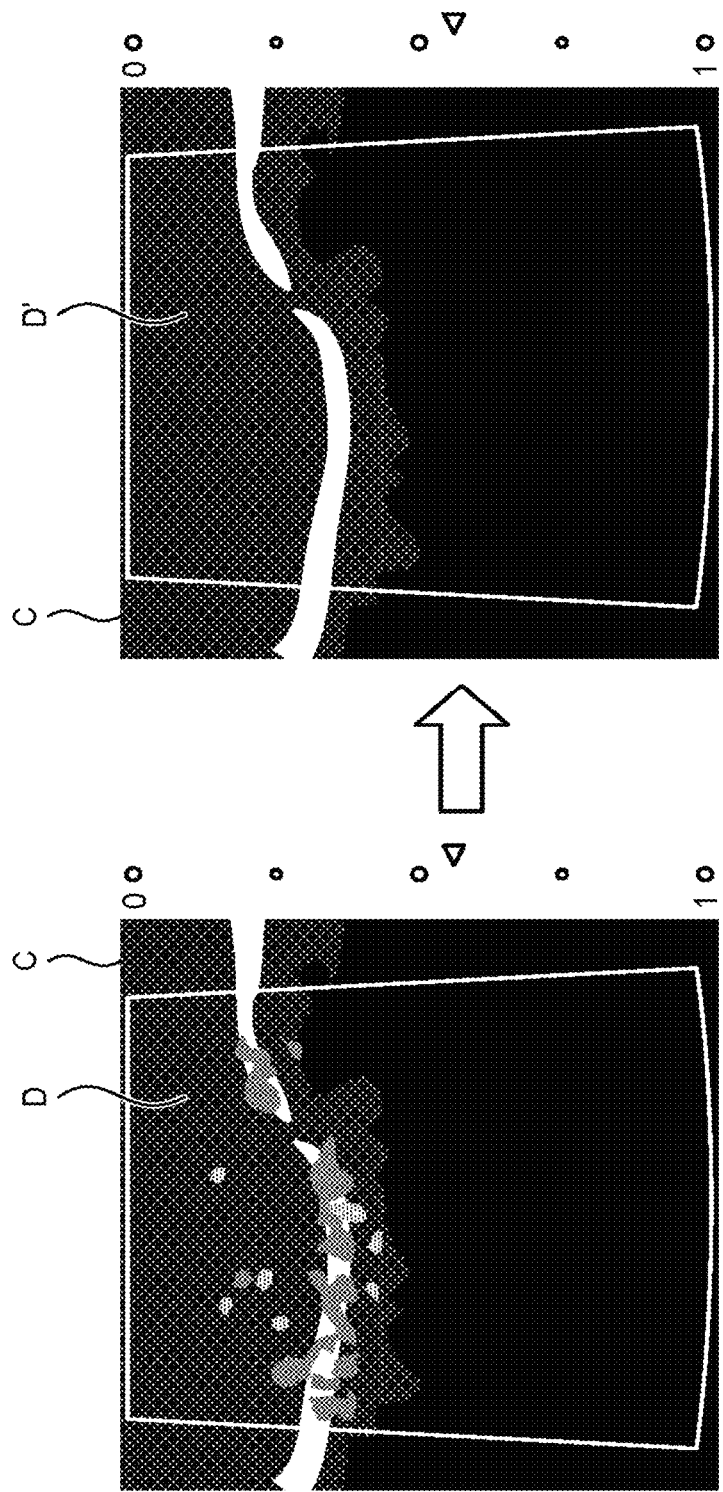

FIG. 8 will now be described. FIG. 8 illustrates image data formed when scanning a range in which there is almost no blood flow but includes the strong reflector while the ultrasound probe 1 is fixed. A left figure in FIG. 8 illustrates Doppler image data D displayed on top of B-mode image data C in which the strong reflector is rendered. The Doppler image data D is generated and displayed without performing the correction processing of the present embodiment. As illustrated in the left figure in FIG. 8, a noise is generated around the strong reflector in the Doppler image data D.

On the other hand, a right figure in FIG. 8 illustrates Doppler image data D' displayed on top of the B-mode image data C. The Doppler image data D' is generated and displayed by the correction processing of the present embodiment. As illustrated in the right figure in FIG. 8, the "noise around the strong reflector" generated in the Doppler image data D is eliminated from the Doppler image data D'. FIGS. 7 and 8 indicate that the correction processing of the present embodiment can avoid the case where the signal derived from the tissue of the strong reflector is displayed as the blood flow.

Figure 9:
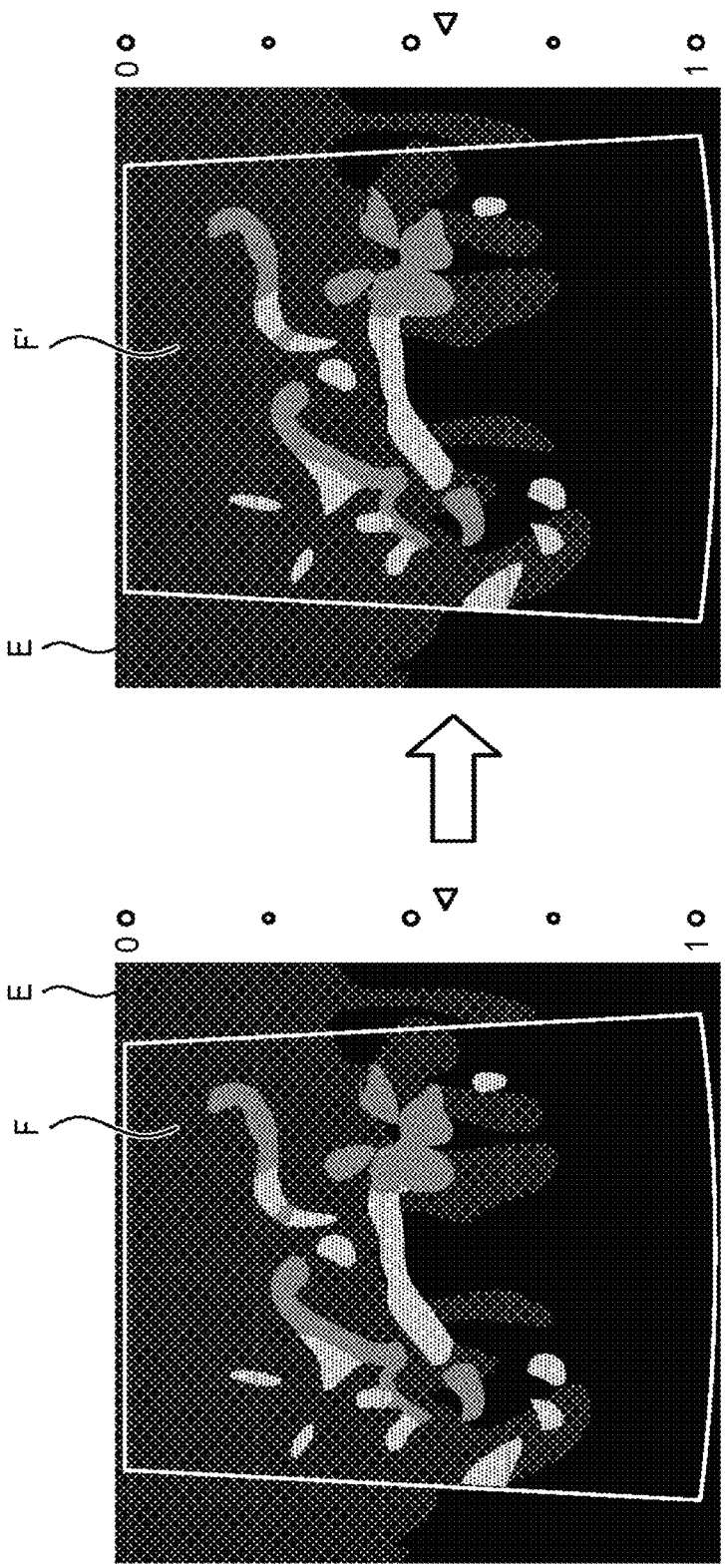

FIG. 9 will now be described. FIG. 9 illustrates image data formed when scanning a range in which there is blood flow but no strong reflector while fixing the ultrasound probe 1. A left figure in FIG. 9 illustrates Doppler image data F displayed on top of B-mode image data E. The Doppler image data F is generated and displayed without performing the correction processing of the present embodiment. The blood flow is rendered in the Doppler image data F as illustrated in the left figure in FIG. 9.

On the other hand, a right figure in FIG. 9 illustrates Doppler image data F' displayed on top of the B-mode image data E. The Doppler image data F' is generated and displayed by the correction processing of the present embodiment. As illustrated in FIG. 9, nearly the same blood flow is rendered in the Doppler image data F and the Doppler image data F'. That is, FIG. 9 indicates that the correction processing of the present embodiment does not affect the blood flow rendered in the Doppler image data F' nor generates another noise.

Figure 10:
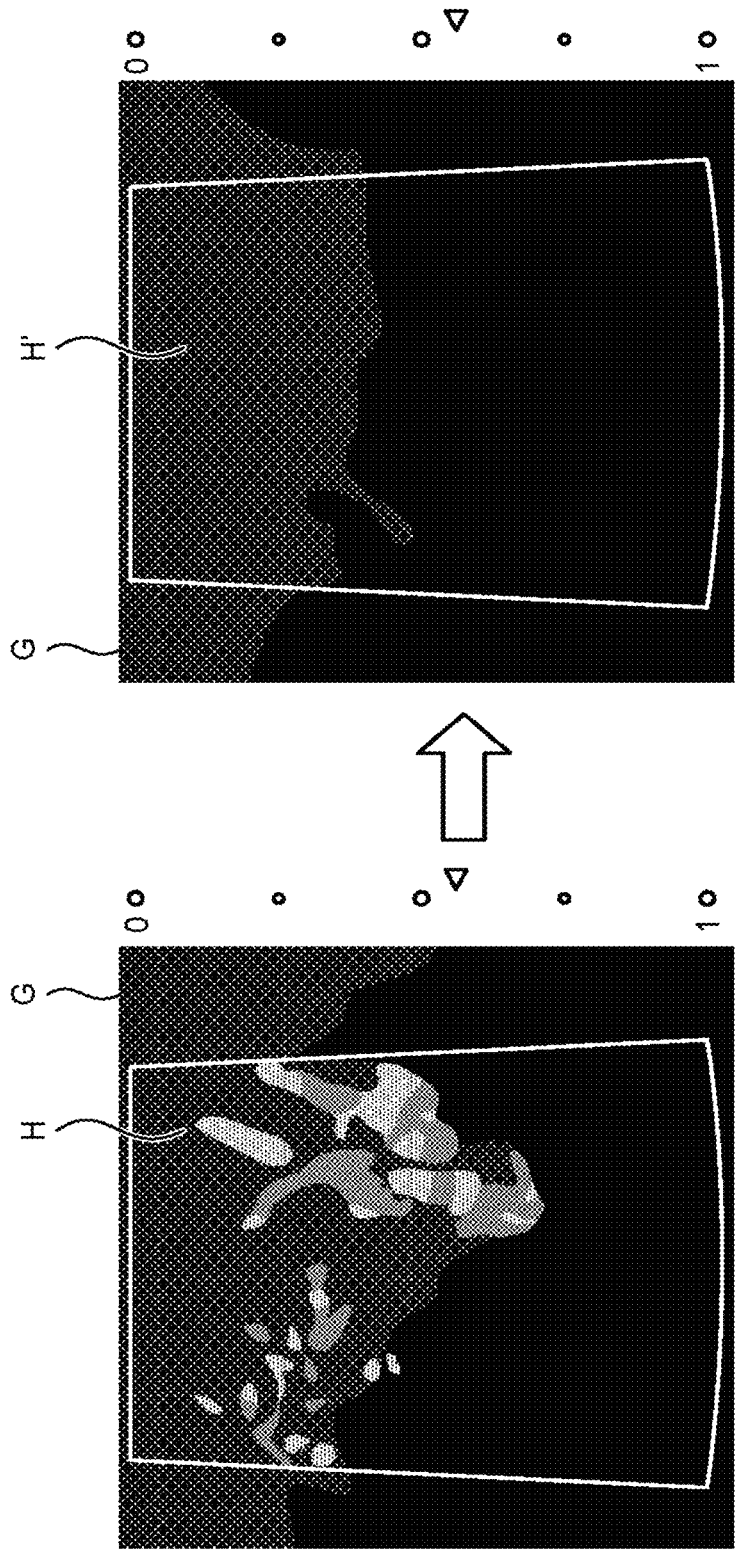

FIG. 10 will now be described. FIG. 10 illustrates image data formed when scanning a range in which there is blood flow but no strong reflector while slightly moving the ultrasound probe 1. A left figure in FIG. 10 illustrates Doppler image data H displayed on top of B-mode image data G. The Doppler image data H is generated and displayed without performing the correction processing of the present embodiment. As illustrated in the left figure in FIG. 10, a noise caused by the movement of the probe is rendered as though it is the blood flow in the Doppler image data H.

On the other hand, a right figure in FIG. 10 illustrates Doppler image data H' displayed on top of the B-mode image data G. The Doppler image data H' is generated and displayed by the correction processing of the present embodiment. As illustrated in the right figure in FIG. 10, the noise caused by the movement of the probe is eliminated from the Doppler image data H'. FIG. 10 indicates that the correction processing of the present embodiment does not generate the noise caused by the slight movement of the probe.

Note that in the present embodiment, the correction may be performed on the output data array "y" by using the correction value to estimate the blood flow information from a corrected output data array. In such case, the corrected output data array is calculated by "ratio" calculated from "P2" of the output data array "y" so that the blood flow information "V, Var, P" is calculated from the corrected output data array.

When the determination circuitry 145 performs the determination processing by using the threshold "V #" in the present embodiment, the processing described with reference to FIG. 4 may include the autocorrelation correction processing but exclude the power correction processing. Moreover, when the determination circuitry 145 performs the determination processing by using the threshold "P #" in the present embodiment, the processing described with reference to FIG. 4 may include the power correction processing but exclude the autocorrelation correction processing. The blood flow information output in the end is determined by the determination circuitry 145, and thus the aforementioned cases are suited for reducing the processing load of the estimation circuitry 143.

The clutter component passing the MTI filter is decreased by the processing performed by the setting circuitry 144 and the estimation circuitry 143. As a result, the strong reflector and the tissue located in the vicinity of the strong reflector are less likely to be observed as the blood flow information in the Doppler image data that is generated by directly using the blood flow information corrected by using the correction value by the estimation circuitry 143. The determination circuitry 145 may thus be adapted to not perform the determination processing in the present embodiment.

Figure 11:
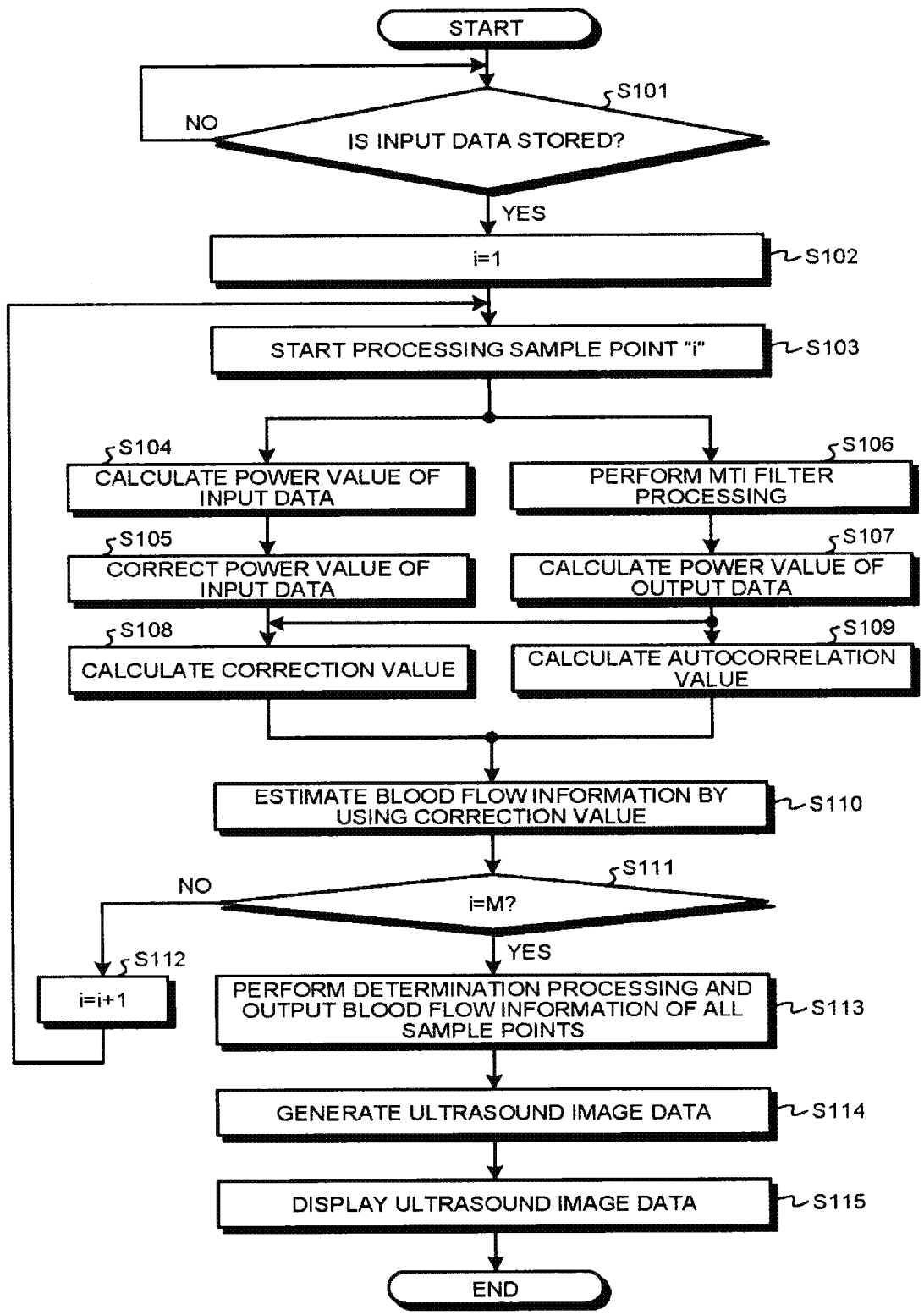
FIG. 11 is a flowchart illustrating an example of processing performed by the ultrasound diagnostic apparatus according to the present embodiment.

Next, FIG. 11 will be referenced to describe an example of processing performed by the ultrasound diagnostic apparatus according to the present embodiment. FIG. 11 is a flowchart illustrating an example of the processing performed by the ultrasound diagnostic apparatus according to the present embodiment. The description in FIG. 11 assumes that the total number of sample points within a scanning range equals "M". Moreover, FIG. 11 is the flowchart illustrating a case where the setting circuitry 144 performs calculation to set the correction value.

As illustrated in FIG. 11, the control circuitry 18 of the ultrasound diagnostic apparatus according to the present embodiment determines whether or not input data of all sample points is stored (step S101). When the input data is not stored (step S101: No), the control circuitry 18 stands by until all the input data is stored.

When the input data is stored (step S101: Yes), on the other hand, the control circuitry 18 sets "i=1" (step S102) and causes the Doppler processing circuitry 14 to start the processing of a sample point "i" (step S103). The setting circuitry 144 first calculates a power value of the input data (such as a maximum power value) (step S104) and corrects the power value of the input data (step S105).

The filter processing circuitry 142 performs the MTI filter processing on the input data to output output data (step S106), and then the estimation circuitry 143 calculates a power value of the output data (such as an average power value) (step S107). The setting circuitry 144 thereafter calculates CDR from the power value of the input data and the power value of the output data, and calculates a correction value on the basis of the CDR (step S108).

The estimation circuitry 143 performs autocorrelation calculation processing by using the output data to calculate an autocorrelation value (step S109). The estimation circuitry 143 then uses the correction value to estimate blood flow information (step S110). That is, the estimation circuitry 143 uses the correction value to correct the power value of the output data and the autocorrelation value, and estimates the blood flow information. The control circuitry 18 thereafter determines whether or not "i=M" (step S111). When "i=M" does not hold (step S111: No), the control circuitry 18 sets "i=i+1" (step S112), returns to step S103, and causes the Doppler processing circuitry 14 to start the processing of the sample point "i".

When "i=M" (step S111: Yes), on the other hand, the determination circuitry 145 performs determination processing and outputs the blood flow information of all the sample points to the image generation circuitry 15 (step S113). The image generation circuitry 15 generates color Doppler image data on the basis of the blood flow information (step S114) so that the display 2 displays the color Doppler image data under control by the control circuitry 18 (step S115), and the processing ends thereafter.

The procedure described with reference to FIG. 11 is merely an example, where the order of each processing illustrated in FIG. 11 can be changed as appropriate. The determination circuitry 145 may perform the determination processing every time the blood flow information of one sample point is estimated, for example.

In the present embodiment, the correction is performed as described above to decrease the value of the blood flow information to the level not visually recognizable by an observer on the basis of the change in power value of the data before and after the MTI filter processing, the value of the blood flow information being estimated from the output data, the source of reflection of which is the strong reflector or the like. The present embodiment can therefore avoid the case where the signal derived from the tissue of the strong reflector is displayed as the blood flow. Moreover, in the present embodiment, it is accurately identified whether a component is derived from the blood flow or the strong reflector on the basis of the change in power value of the data before and after the MTI filter processing, thereby avoiding an erroneous diagnosis caused when the signal derived from the tissue of the strong reflector is displayed as the blood flow. The identification accuracy can be further improved in the present embodiment by employing both the correction processing using the correction value and the determination method using the power value and velocity.

There has been described the case where the correction value is calculated by using the ratio of the power value of the input data to the power value of the output data. Here, the frequency attenuation causes attenuation of the echo intensity from a source of reflection located at a deeper part. The CDR being the ratio of the power value of the input data to the power value of the output data is a value in which the effect of depth information is canceled. The CDR can therefore be used as is as a criterion for identifying whether or not the output data is derived from the clutter component passing the MTI filter.

On the other hand, a difference value between the power value of the input data and the power value of the output data can also be used as the criterion for identifying whether or not the output data is derived from the clutter component passing the MTI filter, for example. That is, the setting circuitry 144 can set the correction value on the basis of the difference value between the power value of the input data and the power value of the output data. The difference value is a value including the effect of the frequency attenuation corresponding to the depth of the sample point. Accordingly, the setting circuitry 144 in using the difference value calculates the correction value by using the depth information along with the power value of the input data and the power value of the output data. The setting circuitry 144 uses the difference value and depth information as input and determines the correction value from a preset LUT, for example. Alternatively, the setting circuitry 144 determines the correction value by performing calculation using an expression to which the difference value and depth information are input to give the correction value, for example. Such variation can also avoid the case where the signal derived from the tissue of the strong reflector is displayed as the blood flow.

The present embodiment is not limited to the case where the setting circuitry 144 sets the correction value on the basis of the ratio or difference of/between the power value of the input data to/and the power value of the output data. The setting circuitry 144 may be adapted to set the correction value by, for example, referring to a LUT in which the correction value is stored in association with the power value of the input data and the power value of the output data and acquiring the correction value corresponding to the input/output data to be processed. In such variation, it is preferred to use "a plurality of LUTs in which the correction value is stored in association with the power value of the input data and the power value of the output data for each depth information". The setting circuitry 144 in this case sets the correction value by referring to the LUT of the depth information corresponding to the input/output data to be processed. Such variation can also avoid the case where the signal derived from the tissue of the strong reflector is displayed as the blood flow.

The present embodiment has described the case where the aforementioned image processing method is executed by the ultrasound diagnostic apparatus. However, the aforementioned image processing method may also be executed by an image processing device which can acquire the reflected wave data (IQ signal) output by the transmission/reception circuitry 11. Moreover, the scanning mode of the ultrasound transmission/reception applied to the aforementioned image processing method can be any scanning mode as long as the mode can collect the data array of the reflected wave data by which the blood flow information can be estimated.

In the aforementioned embodiment, each component of each device illustrated in the drawings is provided as a functional concept and thus does not necessarily have to be physically configured as illustrated in the drawings. That is, a specific mode of distribution and integration of the devices is not limited to what is illustrated in the drawings, where all or a part of the devices can be functionally or physically distributed and/or integrated by an arbitrary unit according to various loads and use status. Moreover, all or an arbitrary part of each processing function performed by each of the devices can be realized by a CPU and a program analyzed/executed by the CPU, or realized by hardware employing wired logic.

Furthermore, the image processing method described in the present embodiment can be implemented by running an image processing program prepared in advance on a computer such as a personal computer or a work station. The image processing program can be distributed through a network such as the Internet. The image processing program can also be executed when a computer reads the program from a computer-readable, non-temporary recording medium such as a hard disk, a flexible disk (FD), a CD-ROM, an MO, a DVD, and a flash memory such as a USB memory and an SD card memory in which the program is recorded.

As described above, according to the present embodiment, there can be avoided the case where the signal derived from the tissue of the strong reflector is displayed as the blood flow.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising:
   filter processing circuitry configured to use, as input data, a data array of reflected wave data of a same location collected by transmitting and receiving an ultrasound pulse multiple times and perform filter processing on the input data to output data, as output data, in which a clutter component is suppressed;
   setting circuitry configured to set a correction value by using a power value of the input data and a power value of the output data;
   estimation circuitry configured to acquire corrected blood flow information by using the output data and the correction value;
   image generation circuitry configured to generate ultrasound image data on the basis of the corrected blood flow information; and
   control circuitry configured to cause the ultrasound image data to be displayed in a display, wherein
   when the power value of the input data is larger than or equal to a predetermined power value, the setting circuitry is configured to:
      (i) correct the power value of the input data to a larger value than an uncorrected power value of the input data, and
      (ii) set the correction value that decreases a value of the corrected blood flow information acquired by the estimation circuitry (a) when a ratio calculated by dividing the corrected power value of the input data by the power value of the output data is larger than or equal to a predetermined ratio, or (b) when a ratio calculated by dividing the power value of the output data by the corrected power value of the input data is smaller than or equal to a predetermined ratio.

2. The ultrasound diagnostic apparatus according to claim 1, wherein the setting circuitry is configured to set the correction value by calculating a ratio of the power value of the input data to the power value of the output data or by calculating a difference between the power value of the input data and the power value of the output data.

3. The ultrasound diagnostic apparatus according to claim 2, wherein
   the setting circuitry is configured to set the correction value that decreases a value of the blood flow information output by the estimation circuitry when a logarithmic value of a ratio calculated by dividing the power value of the input data by the power value of the output data is larger than or equal to a predetermined logarithmic value, or when a logarithmic value of a ratio calculated by dividing the power value of the output data by the power value of the input data is smaller than or equal to a predetermined logarithmic value.

4. The ultrasound diagnostic apparatus according to claim 1, wherein the setting circuitry is configured to set the correction value by using a maximum value of the power value of the input data.

5. The ultrasound diagnostic apparatus according to claim 2, wherein the setting circuitry is configured to set the correction value by using depth information along with the difference between the power value of the input data and the power value of the output data.

6. An image processing device comprising:
   filter processing circuitry configured to use, as input data, a data array of reflected wave data of a same location collected by transmitting and receiving an ultrasound pulse multiple times and perform filter processing on the input data to output data, as output data, in which a clutter component is suppressed;
   setting circuitry configured to set a correction value by using a power value of the input data and a power value of the output data;
   estimation circuitry configured to acquire corrected blood flow information by using the output data and the correction value;
   image generation circuitry configured to generate ultrasound image data on the basis of the corrected blood flow information; and
   control circuitry configured to cause the ultrasound image data to be displayed in a display, wherein
   when the power value of the input data is larger than or equal to a predetermined power value, the setting circuitry is configured to:
      (i) correct the power value of the input data to a larger value than an uncorrected power value of the input data, and
      (ii) set the correction value that decreases a value of the corrected blood flow information acquired by the estimation circuitry (a) when a ratio calculated by dividing the corrected power value of the input data by the power value of the output data is larger than or equal to a predetermined ratio, or (b) when a ratio calculated by dividing the power value of the output data by the corrected power value of the input data is smaller than or equal to a predetermined ratio.

7. An image processing method comprising:
using, as input data, a data array of reflected wave data of a same location collected by transmitting and receiving an ultrasound pulse multiple times and performing filter processing on the input data to output data, as output data, in which a clutter component is suppressed, by filter processing circuitry;
setting a correction value by using a power value of the input data and a power value of the output data by setting circuitry;
acquiring corrected blood flow information by using the output data and the correction value by estimation circuitry;
generating ultrasound image data on the basis of the corrected blood flow information by image generation circuitry; and
causing the ultrasound image data to be displayed in a display by control circuitry, wherein
when the power value of the input data is larger than or equal to a predetermined power value, the setting comprises:
  (i) correcting the power value of the input data to a larger value than an uncorrected power value of the input data, and
  (ii) setting the correction value that decreases a value of the corrected blood flow information acquired by the estimation circuitry (a) when a ratio calculated by dividing the corrected power value of the input data by the power value of the output data is larger than or equal to a predetermined ratio, or (b) when a ratio calculated by dividing the power value of the output data by the corrected power value of the input data is smaller than or equal to a predetermined ratio.

8. An ultrasound diagnostic apparatus comprising:
filter processing circuitry configured to use, as input data, a data array of reflected wave data of a same location collected by transmitting and receiving an ultrasound pulse multiple times and perform filter processing on the input data to output data, as output data, in which a clutter component is suppressed;
setting circuitry configured to set a correction value by using a power value of the input data and a power value of the output data;
estimation circuitry configured to acquire corrected blood flow information by using the output data and the correction value;
image generation circuitry configured to generate ultrasound image data on the basis of the corrected blood flow information; and
control circuitry configured to cause the ultrasound image data to be displayed in a display, wherein
when the power value of the input data is larger than or equal to a predetermined power value, the setting circuitry is configured to:
  (i) correct the power value of the input data to a larger value than an uncorrected power value of the input data, and
  (ii) set the correction value that decreases a value of the corrected blood flow information acquired by the estimation circuitry (a) when a logarithmic value of a ratio calculated by dividing the corrected power value of the input data by the power value of the output data is larger than or equal to a predetermined logarithmic value, or (b) when a logarithmic value of a ratio calculated by dividing the power value of the output data by the corrected power value of the input data is smaller than or equal to a predetermined logarithmic value.

9. An image processing device comprising:
filter processing circuitry configured to use, as input data, a data array of reflected wave data of a same location collected by transmitting and receiving an ultrasound pulse multiple times and perform filter processing on the input data to output data, as output data, in which a clutter component is suppressed;
setting circuitry configured to set a correction value by using a power value of the input data and a power value of the output data;
estimation circuitry configured to acquire corrected blood flow information by using the output data and the correction value;
image generation circuitry configured to generate ultrasound image data on the basis of the corrected blood flow information; and
control circuitry configured to cause the ultrasound image data to be displayed in a display, wherein
when the power value of the input data is larger than or equal to a predetermined power value, the setting circuitry is configured to:
  (i) correct the power value of the input data to a larger value than an uncorrected power value of the input data, and
  (ii) set the correction value that decreases a value of the corrected blood flow information acquired by the estimation circuitry (a) when a logarithmic value of a ratio calculated by dividing the corrected power value of the input data by the power value of the output data is larger than or equal to a predetermined logarithmic value, or (b) when a logarithmic value of a ratio calculated by dividing the power value of the output data by the corrected power value of the input data is smaller than or equal to a predetermined logarithmic value.

10. An image processing method comprising:
using, as input data, a data array of reflected wave data of a same location collected by transmitting and receiving an ultrasound pulse multiple times and performing filter processing on the input data to output data, as output data, in which a clutter component is suppressed, by filter processing circuitry;
setting a correction value by using a power value of the input data and a power value of the output data by setting circuitry;
acquiring corrected blood flow information by using the output data and the correction value by estimation circuitry;
generating ultrasound image data on the basis of the corrected blood flow information by image generation circuitry; and
causing the ultrasound image data to be displayed in a display by control circuitry, wherein
when the power value of the input data is larger than or equal to a predetermined power value, the setting comprises:
  (i) correcting the power value of the input data to a larger value than an uncorrected power value of the input data, and
  (ii) setting the correction value that decreases a value of the corrected blood flow information acquired by the estimation circuitry (a) when a logarithmic value of a ratio calculated by dividing the corrected power value of the input data by the power value of the output data is larger than or equal to a predetermined logarithmic value, or (b) when a logarithmic value of a ratio calculated by dividing the power value of the output data by the corrected power value of the input data is smaller than or equal to a predetermined logarithmic value.

* * * * *